(12) United States Patent
Morimoto et al.

(10) Patent No.: US 9,217,794 B2
(45) Date of Patent: Dec. 22, 2015

(54) SCINTILLATOR ARRAY, AND X-RAY DETECTOR AND X-RAY EXAMINATION DEVICE USING SCINTILLATOR ARRAY

(71) Applicants: Kabushiki Kaisha Toshiba, Tokyo (JP); Toshiba Materials Co., Ltd., Yokohama-Shi (JP)

(72) Inventors: Kazumitsu Morimoto, Kamakura (JP); Akihisa Saito, Yokohama (JP); Yoshitaka Adachi, Yokohama (JP); Masaki Toyoshima, Fujisawa (JP); Eiji Oyaizu, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 14/290,068

(22) Filed: May 29, 2014

(65) Prior Publication Data

US 2014/0301527 A1  Oct. 9, 2014

Related U.S. Application Data

(63) Continuation of application No. PCT/JP2012/007697, filed on Nov. 30, 2012.

(30) Foreign Application Priority Data

Dec. 1, 2011 (JP) .................................. 2011-263927

(51) Int. Cl.
*G01T 1/20* (2006.01)
*G01N 23/04* (2006.01)

(52) U.S. Cl.
CPC ............ *G01T 1/2002* (2013.01); *G01N 23/046* (2013.01); *G01T 1/2006* (2013.01)

(58) Field of Classification Search
CPC ... G01T 1/2002; G01T 1/2006; G01N 23/046
See application file for complete search history.

(56) References Cited

U.S. PATENT DOCUMENTS

| 5,888,647 A | 3/1999 | Yamane |
| 2003/0178570 A1 | 9/2003 | Tsunota et al. |

(Continued)

FOREIGN PATENT DOCUMENTS

| JP | 09-021899 A1 | 1/1997 |
| JP | 2000-180554 A1 | 6/2000 |

(Continued)

OTHER PUBLICATIONS

Extended European Search Report (Application No. 12853509.3) dated Jun. 23, 2015.

(Continued)

*Primary Examiner* — Yara B Green
(74) *Attorney, Agent, or Firm* — Burr & Brown, PLLC (57) ABSTRACT

In one embodiment, a scintillator array includes a plurality of scintillator blocks, and a reflective layer part interposed between the adjacent scintillator blocks. The plurality of scintillator blocks are integrated by the reflective layer part. The reflective layer part includes reflective particles dispersed in a transparent resin. The reflective particles include at least one selected from titanium oxide particles and tantalum oxide particles, and have a mean particle diameter of 2 μm or less. The number of the reflective particles existing per unit area of 5 μm×5 μm of the reflective layer part is in a range of 100 or more and 250 or less.

13 Claims, 5 Drawing Sheets

(56) References Cited

U.S. PATENT DOCUMENTS

2011/0114847 A1   5/2011  Fujieda et al.
2011/0198505 A1*  8/2011  Ishida et al. ............. 250/363.01
2012/0009375 A1*  1/2012  Sakai et al. .................... 428/68

FOREIGN PATENT DOCUMENTS

| | | |
|---|---|---|
| JP | 3104696 B2 | 10/2000 |
| JP | 2004-003970 A1 | 1/2004 |
| JP | 2004-061492 A1 | 2/2004 |
| JP | 2005-283483 | 10/2005 |
| JP | 4266114 B2 | 5/2009 |
| JP | 2009-210415 A1 | 9/2009 |
| JP | 2010-019720 A1 | 1/2010 |
| WO | 2008/090796 | 7/2008 |
| WO | 2010/106884 A1 | 9/2010 |

OTHER PUBLICATIONS

International Search Report and Written Opinion (Application No. PCT/JP2012/007697) dated Feb. 19, 2013.

* cited by examiner

SCINTILLATOR ARRAY, AND X-RAY DETECTOR AND X-RAY EXAMINATION DEVICE USING SCINTILLATOR ARRAY

CROSS-REFERENCE TO RELATED APPLICATIONS

This application is a continuation of prior International Application No. PCT/JP2012/007697 filed on Nov. 30, 2012, which is based upon and claims the benefit of priority from Japanese Patent Application No. 2011-263927 filed on Dec. 1, 2011; the entire contents of all of which are incorporated herein by reference.

BACKGROUND OF THE INVENTION

1. Field of the Invention

An embodiment of the present invention relates to a scintillator array, and an X-ray detector and an X-ray examination device using the scintillator array.

2. Description of Related Art

In fields of medical diagnosis and industrial nondestructive inspection, an X-ray examination device such as an X-ray tomographic photographing device (X-ray CT device) is used. The X-ray CT device has a structure in which an X-ray tube (X-ray source) that radiates fan beam X-rays in a fan shape and an X-ray detector composed of many X-ray detecting elements arranged in parallel are arranged to be opposed to each other with a tomographic surface of a specimen as a center. In the X-ray CT device, the fan beam X-rays are radiated from the X-ray tube to the specimen, and X-ray absorption data transmitted through the specimen is collected by the X-ray detector. The X-ray absorption data collected by the X-ray detector is analyzed by a computer. Concretely, calculation of an X-ray absorptance at individual position in the tomographic surface and reconfiguration of an image according to the X-ray absorptance are performed. Thus, a tomogram of the specimen is reproduced.

As the X-ray detector of the X-ray CT device, a detector having a solid scintillator that emits visible light by excitation with X-rays is frequently used. In the X-ray detector using the solid scintillator, it is easy to increase the number of channels by downsizing the X-ray detecting element, and the resolution of the X-ray CT device can further be increased. Various materials are known as the solid scintillator, and a ceramics scintillator composed of a sintered compact of rare earth oxysulfide such as $Gd_2O_2S$:Pr is particularly effective. The ceramics scintillator composed of the sintered compact of rare earth oxysulfide is excellent in emission efficiency because of large X-ray absorption coefficient and is suitable as a scintillator for X-ray detector because of short afterglow.

For the sintered compact of rare earth oxysulfide phosphor (phosphor ceramics) constituting the ceramics scintillator, various suggestions have been made to improve the optical output, increase the density of the sintered compact, improve the mechanical strength and so on. For example, the optical output is improved by controlling the phosphor amount in the ceramics scintillator (sintered compact). However, the ceramics scintillator is required to further improve optical output. The improvement in optical output of the scintillator leads to a reduced examination time by the X-ray examination device, namely, reduced radiation exposure. To improve the optical output, improvement of a scintillator material can be effective means. Further, in the case where an array structure in which a reflective layer interposed between adjacent scintillator blocks is applied to the ceramics scintillator, improvement of the reflective layer can also be effective means for improving the optical output.

As a conventional scintillator array, there is a known structure in which a radiation shielding plate is interposed between adjacent scintillator blocks and the scintillator blocks are bonded to the radiation shielding plate with an adhesive layer containing titanium oxide powder. The radiation shielding plate and the adhesive layer interposed between the scintillator blocks contribute to the improvement in reflection efficiency of visible light emitted from the scintillator blocks. However, in the case of using both of the radiation shielding plate and the adhesive layer containing titanium oxide powder, an increase in manufacturing cost of the scintillator array is inevitable. Further, in the adhesive layer bonding the scintillator blocks to the radiation shielding plate, fine particles having a mean particle diameter of 1 μm or less are used as the titanium oxide powder. The titanium oxide in a fine particle form is likely to aggregate in the adhesive layer, thereby decreasing the reflection efficiency of the adhesive layer. Also from the point, the radiation shielding plate is used in the conventional scintillator array.

SUMMARY OF THE INVENTION

According to one embodiment of the present invention, a scintillator array includes a plurality of scintillator blocks. and a reflective layer part interposed between the adjacent scintillator blocks to integrate the plurality of scintillator blocks. The reflective layer part includes a transparent resin and reflective particles dispersed in the transparent resin. The reflective particles include at least one selected from the group consisting of titanium oxide particles and tantalum oxide particles, and have a mean particle diameter of 2 μm or less. The number of the reflective particles existing per unit area of 5 μm×5 μm of the reflective layer part is in a range of 100 or more and 250 or less.

DETAILED DESCRIPTION OF INVENTION

Figure 1:
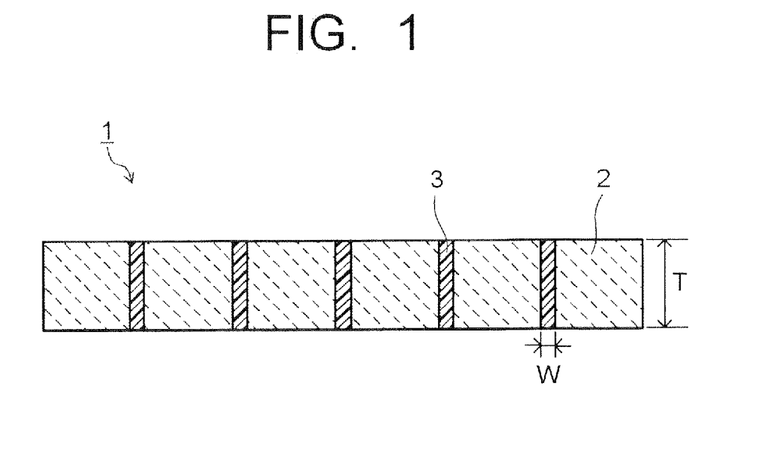
FIG. 1 is a cross-sectional view illustrating a scintillator array in an embodiment.
Figure 2:
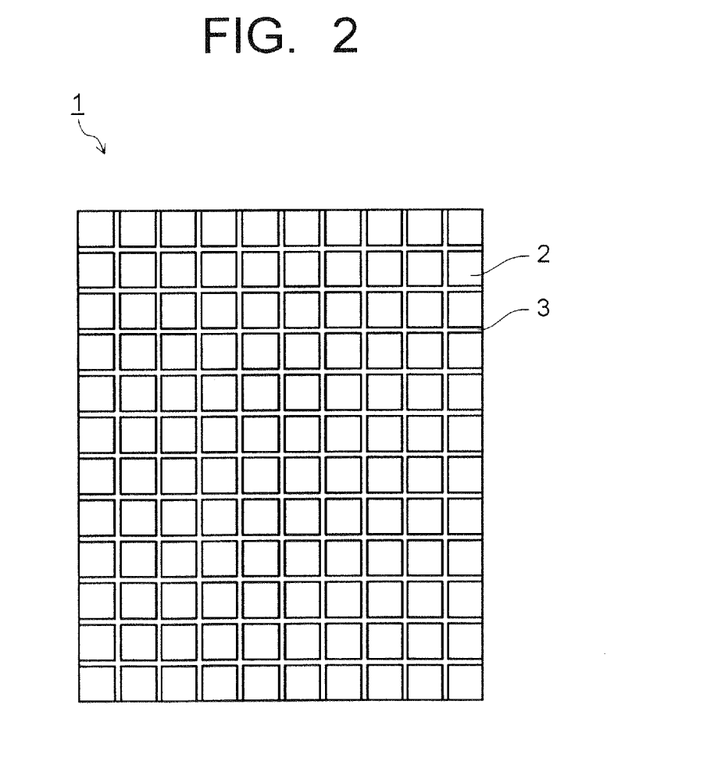
FIG. 2 is a top view illustrating the scintillator array in the embodiment.

Hereinafter, a scintillator array, an X-ray detector, and an X-ray examination device in an embodiment will be described referring to the drawings. FIG. 1 and FIG. 2 are views illustrating a configuration of the scintillator array in the embodiment. In these drawings, 1 denotes a scintillator array, 2 denotes a scintillator block, and 3 denotes a reflective layer part. The scintillator array 1 has a plurality of scintillator blocks 2. Between adjacent scintillator blocks 2, the reflective layer part 3 is interposed. The reflective layer part 3 is directly bonded to the adjacent scintillator blocks 2. The plurality of scintillator blocks 2 are integrated by the reflective layer part 3 bonded thereto. Namely, the scintillator array 1 has a structure in which a plurality of scintillator blocks 2 are integrated by the reflective layer parts 3.

The scintillator array 1 may have either a structure in which a plurality of scintillator blocks 2 are arrayed in a row or a structure in which a predetermined number of a plurality of scintillator blocks 2 are two-dimensionally arrayed in a longitudinal direction and in a lateral direction as illustrated in FIG. 2. The scintillator array 1 has a multichannel structure. In the case where the plurality of scintillator blocks 2 are two-dimensionally arrayed, the reflective layer part 3 is provided between the scintillator blocks 2 in each of the longitudinal direction and the lateral direction. The number of the scintillator blocks 2 is appropriately set according to the structure, the resolution and the like of the X-ray detector.

The reflective layer part 3 has reflective particles having a mean particle diameter of 2 μm or less and a transparent resin layer. The reflective particles are dispersed in the transparent resin layer. The reflective particles include at least one kind selected from among titanium oxide particles and tantalum oxide particles. Examples of the reflective particles include titanium oxide particles, tantalum oxide particles, aluminum oxide particles, magnesium oxide particles and so on. The reflective layer part 3 in the embodiment contains at least one kind selected from among titanium oxide particles and tantalum oxide particles as the reflective particles, as an essential component.

The titanium oxide particles and the tantalum oxide particles are high in reflectance of light emitted from the scintillator block 2 excited with X-rays and therefore contained in the reflective layer part 3 as the essential component. The titanium oxide is preferably a titanium dioxide ($TiO_2$). The tantalum oxide is preferably a ditantalum pentoxide ($Ta_2O_5$). Use of them makes it possible to further increase the reflectance by the reflective layer part 3. Since the titanium dioxide ($TiO_2$) and the ditantalum pentoxide ($Ta_2O_5$) are high in reflectance of light in a visible spectrum of 450 nm to 700 nm, and thus can improve the optical output of the scintillator array 1 regardless of the material quality of the scintillator block 2.

The reflective particles have a mean particle diameter of 2 μm or less. The mean particle diameter of the reflective particles is preferably 1 μm or less, and more preferably 0.4 μm or less. If the mean particle diameter of the reflective particles exceeds 2 μm, it becomes difficult to control the dispersion state in the reflective layer part 3. In order to control the number of the reflective particles in a small unit area of 5 μm×5 μm, the reflective particles having a mean particle diameter of 2 μm or less are used. Though the lower limit value of the mean particle diameter of the reflective particles is not particularly limited, but is preferably 0.01 μm or more in consideration of the manufacturability of the reflective particles.

In the scintillator array 1 in the embodiment, the number of the reflective particles existing in an arbitrary unit area of 5 μm×5 μm of the reflective layer part 3 is in a range of 100 to 250. Namely, when measuring the number of the reflective particles existing in the arbitrary unit area (5 μm×5 μm) of the reflective layer part 3, the scintillator array 1 includes the reflective layer part 3 having a number of reflective particles in a range of 100 to 250. By controlling the number of the reflective particles in a small area that is a unit area of 5 μm×5 μm, the reflection efficiency by the reflective layer part 3 of the visible light emitted from the scintillator block 2 can be increased. By increasing the reflection efficiency by the reflective layer part 3, it becomes possible to improve the light intensity from the scintillator block 2 and accordingly improve the optical output of the scintillator array 1.

If the number of the reflective particles existing in the arbitrary unit area (5 μm×5 μm) of the reflective layer part 3 is less than 100, the reflective layer part 3 partially lacks for the reflective particles and therefore fails to uniformly increase the optical output of the scintillator array 1. In the case where the number of the reflective particles exceeds 250, the reflective layer part 3 has an excessive number of reflective particles and therefore fails to uniformly increase the optical output of the scintillator array 1. The number of the reflective particles existing per unit area (5 μm×5 μm) of the reflective layer part 3 is preferably in a range of 150 to 200. The number of the reflective particles existing per unit area (5 μm×5 μm) is measured by photographing macrograph (SEM image) of an arbitrary cross section of the reflective layer part 3. The magnification of the macrograph is set to 4000-fold or more. The number of the reflective particles per unit area (5 μm×5 μm) is counted in the macrograph. An aggregate made by reflective particles in contact is counted as one reflective particle. The reflective particles may be observed also using plane analysis of EPMA.

In the reflective layer part 3 containing the reflective particles having a mean particle diameter of 2 μm or less, an area ratio of aggregates of the reflective particles per unit area of 10 μm×10 μm is preferably 40% or less (including 0%). If the area ratio of aggregates exceeds 40%, the reflective particles partially increase and the ratio of the transparent resin inversely partially decreases. If the ratio of the transparent resin in the reflective layer part 3 partially decreases, the adhesive force of the reflective layer part 3 to the scintillator block 2 decreases. Due to the decrease in the adhesive force between the scintillator blocks 2 by the reflective layer part 3, the flexural strength as the scintillator array 1 decreases. The decrease in the flexural strength degrades the handling property of the scintillator array 1. The area ratio of aggregates per unit area (10 μm×10 μm) is more preferably 10% or less (including 0%). Controlling the area ratio of aggregates makes it possible to increase the reflection efficiency of the reflective layer parts 3 while improving the strength of the scintillator array 1.

Further, by controlling the number of the reflective particles per unit area (5 μm×5 μm) in the reflective layer part 3 and controlling the ratio of aggregates of the reflective particles per unit area (10 μm×10 μm), the contraction rate of the reflective layer part 3 when the transparent resin is hardened is made uniform. This makes it possible to suppress warpage of the scintillator array 1 in a manufacture process and after manufacture. This leads to a reduction in load in a warpage repair process for the scintillator array 1. It is also possible to suppress positional displacement (pitch displacement) of the scintillator block 2 when the transparent resin is hardened. The transparent resin constituting the reflective layer part 3 is preferably an epoxy resin. The transparent resin is not particularly limited, but in the case where the transparent resin containing the reflective particles is filled between the scintillator blocks 2 two-dimensionally arrayed as illustrated in FIG. 2, it is preferable to apply a fluid resin and then harden the resin. The resin having such characteristics can be an epoxy resin.

The width of the reflective layer part 3 (the distance (width W in FIG. 1) between the adjacent scintillator blocks 2) is preferably in a range of 10 μm to 100 μm. The width of the reflective layer part 3 is not particularly limited as long as it has a shape to allow the scintillator block 2 to be arranged on a pixel of a later-described photoelectric conversion element. However, if the width of the reflective layer part 3 is less than 10 μm, the reflective layer part 3 deteriorates in function as the adhesive layer and is thus more likely to decrease in adhesion strength to the scintillator block 2. This may cause a decrease in the strength of the scintillator array 1. If the width of the reflective layer part 3 exceeds 100 μm, the scintillator array 1 becomes large more than necessary. The width of the reflective layer part 3 is more preferably in a range of 20 μm to 80 μm. In the scintillator array 1 illustrated in FIG. 2, the width of the reflective layer part 3 does not need to be the same between the longitudinal direction and the lateral direction.

Furthermore, the reflective layer part 3 is preferably reduced in ratio of voids existing therein. More specifically, the existing ratio of voids in a cross section in the thickness direction (a thickness T direction in FIG. 1) of the reflective layer part 3 is preferably 1% or less. It is most preferable that no void (an existing ratio of 0%) exists in the reflective layer part 3. However, in the case where the reflective layer part 3 is provided to have the small width as describe above, it is a heavy production load to completely eliminate voids in the reflective layer part 3. In the reflective layer part 3 in the embodiment, the number of the reflective particles in a small area (unit area of 5 μm×5 μm) is controlled, so that if the existing ratio of voids in the thickness direction is about 1%, the reflective layer part 3 can be used as having a function as the adhesive layer. The existing ratio of voids in the cross section in the thickness direction is more preferably 0.5% or less, and further preferably 0.1% or less.

The existing ratio of voids in the cross section in the thickness direction of the reflective layer part 3 is measured as follows. First, the reflective layer part 3 is cut in the thickness direction to obtain a cross section. The cutting of the reflective layer part 3 is performed at an arbitrary position. In the arbitrary cross section of the reflective layer part 3, the lengths of individual voids existing in the cross section in the thickness direction of the reflective layer part 3 are obtained, and the lengths of the voids are summed up. From the total length of the voids (total length of the individual voids in the thickness direction of the reflective layer part 3) and the thickness of the reflective layer part 3, the existing ratio of voids is obtained by the following expression.

Ratio of voids [%]=(total length of voids/thickness of reflective part)×100

The scintillator block 2 is preferably a solid scintillator composed of a single crystal body or a polycrystal body of a metal oxide, a metal sulfide, a metal oxysulfide. A metal oxide phosphor constituting the solid scintillator can be a metal oxide having a garnet structure. A garnet-type metal oxide is preferably aluminum garnet having a composition expressed by the following expression (1).

Here, α and β are numbers (atomic ratios) satisfying 0<α≤0.5, 0<β≤0.5, α≤β<0.85, γ is a number (atomic ratio) satisfying 0.0001≤γ≤0.1, x is a number (atomic ratio) satisfying 0<x<1, a is a number (atomic ratio) satisfying 4.8≤a≤5.2, b is a number (atomic ratio) satisfying 11.6≤b≤12.4.

The metal sulfide phosphor constituting the solid scintillator is preferably a rare earth sulfide and can be, for example, a complex sulfide such as NaGdS$_2$:Bi. The metal oxysulfide phosphor can be a rare earth oxysulfide. The rare earth oxysulfide is preferably a gadolinium oxysulfide having a composition expressed by the following expression (2).

Gd$_2$O$_2$S:Pr$_a$ (2)

Here, a is an activation amount of praseodymium (Pr) to 1 mole of gadolinium oxysulfide (Gd$_2$O$_2$S) and preferably in a range of 0.0001 mole to 0.005 mol.

The scintillator block 2 composed of the single crystal body or polycrystal body of the above-described metal oxide, metal sulfide, metal oxysulfide is likely to emit light when excited with X-rays and is high in optical sensitivity, and is therefore suitable for an X-ray detector. Further, the above-described material is stable with respect to heat when hardening the transparent resin such as the epoxy resin, and is therefore suitable as the constituent material of the scintillator blocks 2 that are to be bonded and integrated by the reflective layer part 3. The scintillator block 2 more preferably contains at least one kind selected from among a sintered compact of aluminum garnet having the composition expressed by the expression (1) and a sintered compact of gadolinium oxysulfide having the composition expressed by the expression (2).

The thickness of the scintillator block 2 is preferably in a range of 0.5 mm to 3 mm, and more preferably in a range of 1 mm to 2 mm. If the thickness of the scintillator block 2 is less than 0.5 mm, the X-ray component transmitted through the scintillator block 2 increases and thereby may cause a decrease in optical output. The thickness of the scintillator block 2 exceeding 3 mm not only provides no more improvement in optical output but also becomes a factor of increasing the manufacturing cost. The lengths in the longitudinal direction and the lateral direction of the scintillator block 2 are not particularly limited. In the case where the scintillator block 2 is of a bar-type (rod shape), the length in the longitudinal direction is preferably in a range of 20 mm to 50 mm, and the length in the lateral direction is preferably in a range of 1 mm to 3 mm. When the scintillator blocks 2 are two-dimensionally arrayed as illustrated in FIG. 2, both of the lengths in the longitudinal direction and the lateral direction of the scintillator block 2 are preferably in a range of 0.5 mm to 2 mm.

The scintillator block 2 preferably has a surface roughness in arithmetic mean roughness Ra (JIS B 0601-2001) of 5 μm or less. Setting the surface of the scintillator block 2 to a flat surface with a surface roughness (Ra) of 5 μm or less makes it possible to suppress irregular reflection of X-rays. Namely, the incident amount of X-rays into the scintillator block 2 can be increased. This increases the measurement accuracy of the X-rays by the scintillator block 2. The surface roughness (Ra) of the scintillator block 2 is preferably 1 μm or less, and more preferably 0.1 μm or less.

The reflective layer part 3 preferably has a reflectance of 93% or more to light with a wavelength of 510 nm. Further, the reflective layer part 3 preferably has a reflectance of 90% or more to light with a wavelength of 670 nm. The X-ray detector is intended to cause the scintillator block 2 to emit visible light by exciting the scintillator block 2 with the X-rays and converts the visible light into an electric signal by the photoelectric conversion element and detects it. Accordingly, the reflective layer part 3 is required to have a high reflectance to the light with a wavelength of 450 nm to 700 nm that is the visible spectrum. The reflective layer part 3 more preferably has a reflectance to the light in the whole visible spectrum of 90% or more. The above-described gadolinium oxysulfide phosphor has large emission peaks respectively in a range of 500 nm to 520 nm and a range of 650 nm to 680 nm as the light emission spectra when excited with the X-rays. Accordingly, improving the reflectance to the light in the above wavelength ranges of the reflective layer part 3 makes it possible to further increase the optical output of the scintillator array 1.

Figure 3:
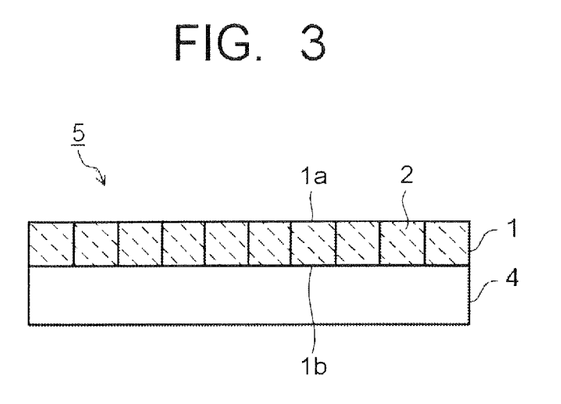
FIG. 3 is a cross-sectional view illustrating an X-ray detector in the embodiment.
Figure 4:
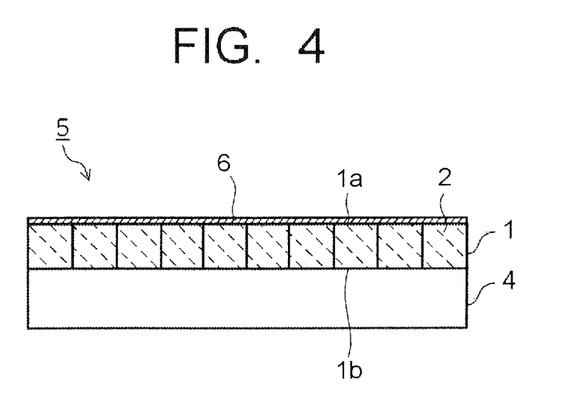
FIG. 4 is a cross-sectional view illustrating a modified example of the X-ray detector in the embodiment.

Next, the X-ray detector and the X-ray examination device in the embodiment will be described referring to the drawings. FIG. 3 and FIG. 4 are views illustrating a configuration of the X-ray detector in the embodiment. In these drawings, 4 denotes a photoelectric conversion element, 5 denotes an X-ray detector, and 6 denotes a surface reflective layer. The scintillator array 1 has an X-ray incident surface 1a and has, on the opposite side to the X-ray incident surface 1a, a surface 1b on which the photoelectric conversion element 4 is integrally mounted. As the photoelectric conversion element 4, for example, a photodiode is used. The photoelectric conversion element 4 is arranged at a position corresponding to the scintillator blocks 2 constituting the scintillator array 1. As illustrated in FIG. 4, the surface reflective layer 6 may be provided on the X-ray incident surface 1a of the scintillator array 1. They constitute the X-ray detector 5.

The surface reflective layer 6 may be provided not only on the X-ray incident surface 1a of the scintillator array 1 but also on the mounting surface 1b for the photoelectric conversion element 4. Further, the surface reflective layer 6 may be provided on both the X-ray incident surface 1a and the element mounting surface 1b of the scintillator array 1. Providing the surface reflective layer 6 on the scintillator array 1 makes it possible to further improve the reflection efficiency of the visible light emitted from the scintillator blocks 2 and accordingly increase the optical output of the scintillator array 1. For the surface reflective layer 6, a mixture of the reflective particles and the transparent resin, a lacquer-based coating material or the like is used. The mixture of the reflective particles and the transparent resin preferably has a dispersion state of the reflective particles as in the reflective layer parts 3. The thickness of the surface reflective layer 6 is preferably in a range of 50 μm to 250 μm. If the thickness of the surface reflective layer 6 is less than 50 μm, the surface reflective layer 6 fails to obtain sufficient improvement effect of the reflection efficiency. If the thickness of the surface reflective layer 6 exceeds 250 μm, the surface reflective layer 6 decreases in the amount of the X-rays transmitted therethrough to decrease in detection sensitivity.

Figure 5:
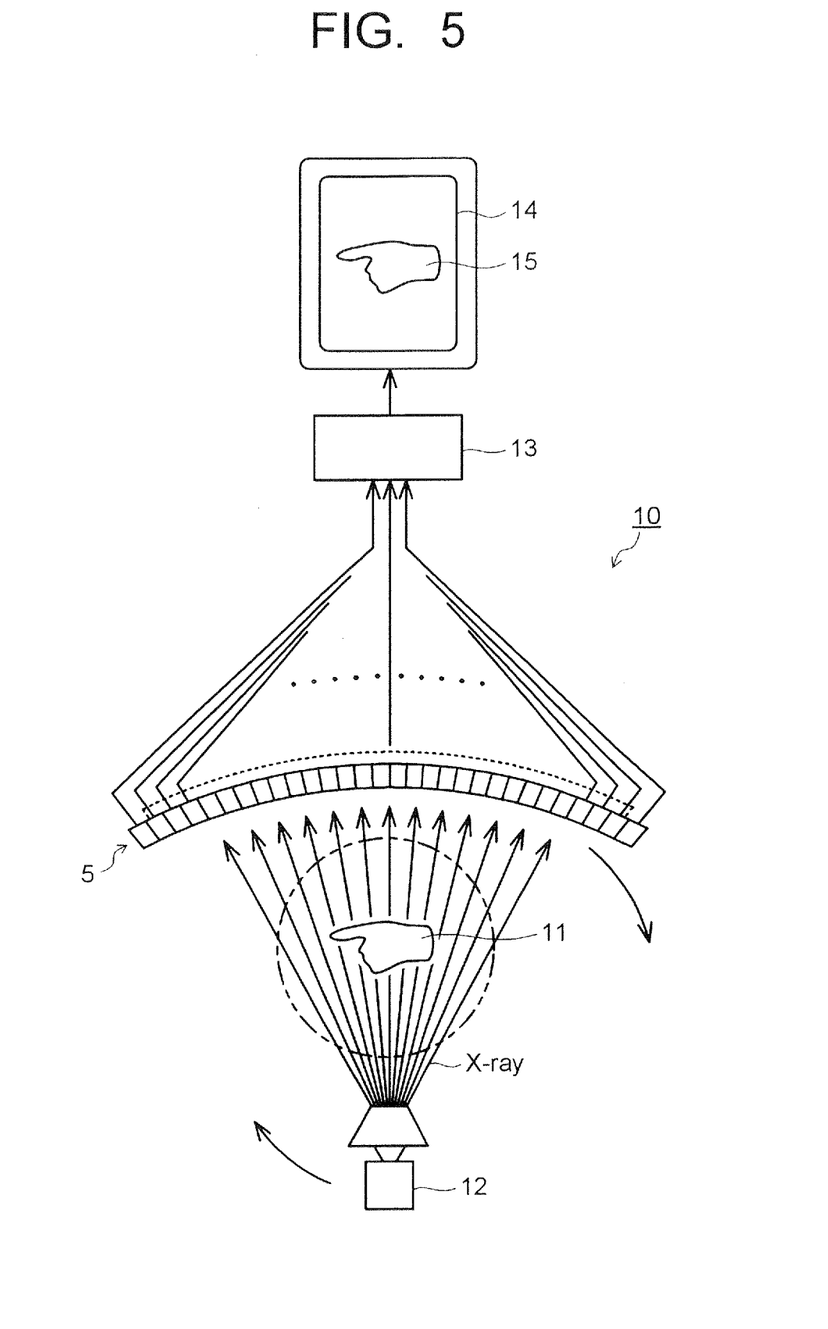
FIG. 5 is a conceptual view illustrating an X-ray examination device in the embodiment.

FIG. 5 illustrates an X-ray CT device 10 being one example of the X-ray examination device in the embodiment. In FIG. 5, 10 denotes the X-ray CT device, 11 denotes a specimen, 12 denotes an X-ray tube, 13 denotes a computer, 14 denotes a display, and 15 denotes a specimen image. The X-ray CT device 10 includes the X-ray detector 5 in the embodiment. The X-ray detector 5 is pasted to an inner wall surface of a cylinder in which an photographing region of the specimen 11 is to be laid out. Almost at the center of an arc of the cylinder to which the X-ray detector 5 is pasted, the X-ray tube 12 that emits X-rays is installed. Between the X-ray detector 5 and the X-ray tube 12, the specimen 11 is arranged. On the X-ray incident surface side of the X-ray detector 5, a not illustrated collimator is provided.

The X-ray detector 5 and the X-ray tube 12 are configured to rotate around the specimen 11 while photographing with the X-rays. Image information of the specimen 11 is three-dimensionally collected from different angles. The signals obtained by the X-ray photographing (electric signals converted by the photoelectric conversion elements) are processed by the computer 13 and displayed on the display 14 as the specimen image 15. The specimen image 15 is, for example, a tomogram of the specimen 11. Using the scintillator array 1 in which the scintillator blocks 2 are two-dimensionally arrayed as illustrated in FIG. 2 makes it possible to configure a multi-tomogram type X-ray CT device 10. In this case, a plurality of tomograms of the specimen 11 can be simultaneously photographed and, for instance, three-dimensionally draw the photographing results.

The X-ray CT device 10 illustrated in FIG. 5 includes the X-ray detector 5 having the scintillator array 1 in the embodiment. As described above, the scintillator array 1 in the embodiment has an excellent optical output because of its high reflection efficiency for the visible light emitted from the scintillator blocks 2 based on the configuration and so on of the reflective layer parts 3. Using the X-ray detector 5 having the scintillator array 1 makes it possible to shorten the photographing time by the X-ray CT device 10. As a result, it is possible to shorten the radiation exposure time of the specimen 11 and realize reduced radiation exposure. The X-ray examination device (X-ray CT device 10) in the embodiment is applicable not only to the X-ray examination for medical diagnosis of a human body but also to the X-ray examination for animals, the X-ray examination for industrial usage and so on.

The scintillator array 1 in the embodiment is manufactured as follows for instance. Hereinafter, a method of efficiently manufacturing the scintillator array 1 in the embodiment will be described. The manufacturing method of the scintillator array 1 in the embodiment is not limited to this. The scintillator array 1 only needs to have the above-described configuration and is not limited to the manufacturing method.

First, reflective particles having a mean particle diameter of 2 μm or less are prepared. The reflective particles preferably have a particle size distribution having a peak in a range of 0.2 μm to 0.3 μm. To prevent aggregation of the reflective particles in the reflective layer parts 3, it is preferable to break beforehand the aggregates of the reflective particles by an ultrasonic vibrator or the like. The impurity component amount in the reflective particles is preferably 1 mass % or less. Next, a transparent resin is prepared. The transparent resin is not particularly limited as long as it transmits light in the scintillator block 2, but is preferably a thermosetting resin such as an epoxy resin, a silicone resin or the like.

The reflective particles and the transparent resin are mixed together. To cause a predetermined number of reflective particles to exist in the transparent resin, it is preferable to mix the reflective particles and the transparent resin in consideration of the ratio between the volume of the reflective particles and the volume of the transparent resin. It is preferable to mix the reflective particles and the transparent resin by using three rolls. The three rolls constitute a mixing machine using three rolls as the term indicates. Since the three rolls are simultaneously moved for mixing, the mixing directions are a plurality of directions to hardly form aggregates during the mixing process. The mixing process using the three rolls is preferably performed for 10 hours or more. Further, it is also effective to mix an organic solvent to decrease the viscosity of the transparent resin, as necessary, for mixing. When mixing the reflective particles and the transparent resin, it is preferable not to mix all of the reflective particles at once but to mix the reflective particles little by little (for example, by a third of them every time).

A plurality of scintillator blocks 2 processed in a predetermined shape are arranged at fixed intervals. The mixture of the reflective particles and the transparent resin (hereinafter, described as a resin mixture) is filled in a gap between adjacent scintillator blocks 2. By setting the viscosity of the resin mixture to 0.5 Pa·s to 2.5 Pa·s (500 cps to 2500 cps), the resin mixture can be smoothly filled in the gap between the scintillator blocks 2. If the viscosity of the resin mixture is less than 0.5 Pa·s (500 cps), the resin mixture is too low in viscosity and may fail to satisfactorily control the dispersion state of the reflective particles when the resin mixture is hardened. If the viscosity of the resin mixture exceeds 2.5 Pa·s (2500 cps), the resin mixture is too high in viscosity and becomes difficult to be uniformly filled in the gap between the scintillator blocks 2.

The filling process is preferably performed in a vacuum. This makes it possible to suppress formation of voids in the reflective layer parts 3. The degree of vacuum during the filling is preferably 4 kPa (30 Torr) or less. In a vacuum atmosphere of 4 kPa or less, it is easy to control the existing ratio of voids in the thickness direction of the reflective layer part 3 to 0.1% or less. Preferably, the surface of the scintillator block 2 has been processed flat to have a surface roughness (Ra) of 5 μm or less. After the resin mixture is filled, a heat treatment for hardening the transparent resin is performed. The heat treatment is preferably performed at a temperature in a range of, for example, 80° C. to 160° C. according to the curing temperature of the transparent resin. The scintillator block 2 composed of the gadolinium oxysulfide sintered compact or the aluminum garnet sintered compact is preferable because it does not change in quality during the heat treatment process. To prevent the reflective particles from depositing in the transparent resin before hardened, it is preferable to perform the heat treatment within three hours after the transparent resin mixed with the reflective particles is filled.

Figure 6:
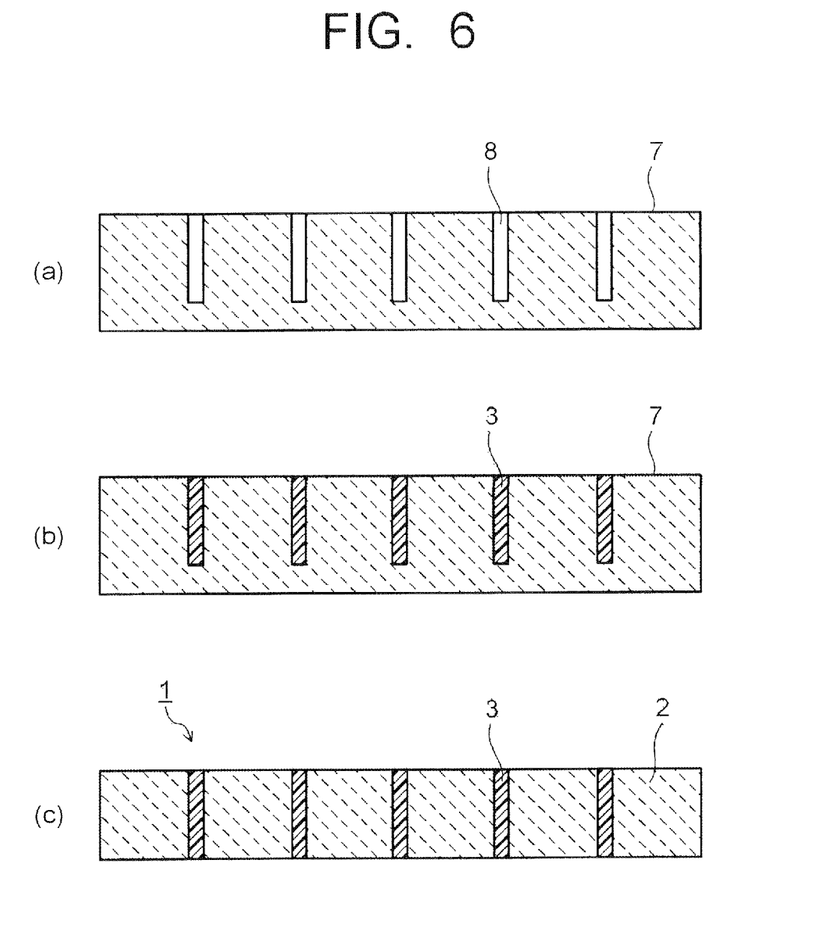
FIG. 6 is a cross-sectional view illustrating an example of a manufacturing process of the scintillator array in the embodiment.

Another method of filling the transparent resin mixed with the reflective particles (resin mixture) will be described referring to FIG. 6. In FIG. 6, 7 denotes a scintillator block base body, and 8 denotes a groove part. The scintillator block base body 7 is a plate-like base body before it is cut into individual scintillator blocks 2. As illustrated in FIG. 6(*a*), the groove parts 8 being positions where the reflective layer parts 3 are to be formed are formed in the scintillator block base body 7. The groove parts 8 are formed by processing the scintillator block base body 7 down to a fixed depth in a manner not to penetrate to the rear surface of the scintillator block base body 7. Grooving is performed on the scintillator block base body 7 by providing longitudinal grooves and lateral grooves in the scintillator block base body 7 to finally obtain the scintillator blocks 2 in a predetermined size.

Next, as illustrated in FIG. 6(*b*), the resin mixture is filled into the groove parts 8 provided in the scintillator block base body 7. Setting the viscosity of the resin mixture to a range of 0.5 Pa·s to 2.5 Pa·s makes it possible to smoothly fill the resin mixture into the groove parts 8. Further, filling the resin mixture into the groove parts 8 in a vacuum can suppress generation of voids. The degree of vacuum during the filling is preferably 4 kPa or less. In the vacuum atmosphere of 4 kPa or less, the existing ratio of voids in the thickness direction of the reflective layer parts 3 can be easily controlled to 0.1% or less.

It is also effective to fill the transparent resin mixed with the reflective particles (resin mixture) into the groove parts 8 using a centrifuge. By utilizing the centrifugal force by the centrifuge, the resin mixture can be uniformly filled into many groove parts 8 provided in the scintillator block base body 7. The centrifuge is effective in the case of filling the resin mixture into many scintillator block base bodies 7 at once and in the case of filling the resin mixture into a large scintillator block base body 7. Further, it is also effective to fill the resin mixture in a vacuum. In the case of filling the resin mixture using the centrifuge, it is preferable to set the rotation speed of the centrifuge to 500 rpm to 3000 rpm, and set the rotation time to 30 minutes or more.

In the case of filling the resin mixture into the groove parts 8 by applying the centrifugal force, the voids contained in the transparent resin are discharged to the outside by the centrifugal force. In this event, if the viscosity of the resin mixture exceeds 2.5 Pa·s, the voids are difficult to discharge to the outside. If the viscosity of the resin mixture is less than 0.5 Pa·s, the resin mixture may run down to the outside of the scintillator block base body 7 when the centrifugal force is made acts thereon. The viscosity of the resin mixture is preferably in a range of 0.5 Pa·s to 2.5 Pa·s. Further, to uniformly fill the resin mixture into the groove parts 8 provided in the scintillator block base body 7, a rotation speed at a certain degree is required. The rotation speed of the centrifuge is preferably 500 rpm or more. If the rotation speed is too high, the resin mixture may run down to the outside of the scintillator block base body 7. The rotation speed of the centrifuge is preferably 3000 rpm or less.

As described above, by adjusting the viscosity of the transparent resin containing the reflective particles (resin mixture), the degree of vacuum during the filling process, the number of the rotations and the rotation time of the centrifuge and so on, the resin mixture can be uniformly filled into the groove parts 8 provided in the scintillator block base body 7. This makes it possible to satisfactorily control the number of the reflective particles per unit area (5 μm×5 μm) in the reflective layer parts 3. Further, the existing ratio of the voids in the thickness direction of the reflective layer parts 3 can be set to 1% or less, further to 0.1% or less, furthermore to 0% (detection limit or less).

Next, the transparent resin (for example, thermosetting resin composition) in the resin mixture filled in the groove parts 8 is hardened. By hardening the transparent resin, the scintillator array base body 7 having the reflective layer parts 3 is formed. Then, as illustrated in FIG. 6(*c*), polishing is performed on the scintillator array base body 7 having the reflective layer parts 3 to thereby segment the scintillator array base body 7 into individual scintillator blocks 2 and simultaneously process the reflective layer parts 3 so as to have a shape penetrating from the front to the rear of the scintillator array 1. The polishing may be performed on one surface or both surfaces of the scintillator array base body 7. The polishing of the scintillator array base body 7 is preferably performed so that the surface roughness (Ra) of the scintillator blocks 2 becomes 5 μm or less.

Figure 7:
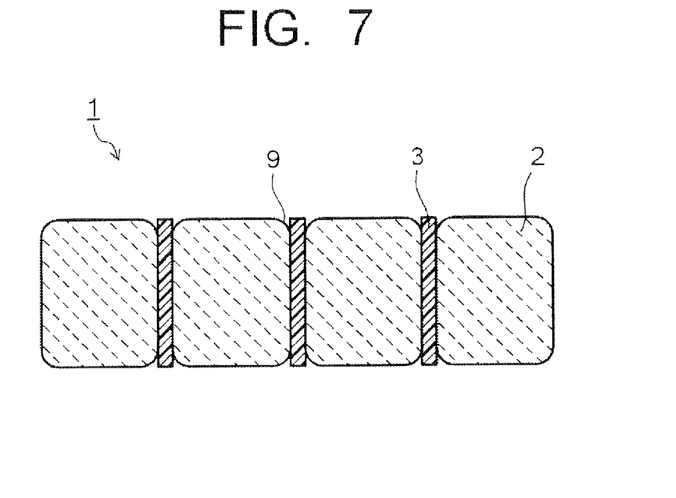
FIG. 7 is a cross-sectional view illustrating another example of the scintillator array in the embodiment.

When polishing the surface of the scintillator array base body 7, an R-shaped portion may be formed at end portions of the scintillator blocks 2. A scintillator array 1 provided with scintillator blocks 2 having the R-shaped portions at end portions is illustrated in FIG. 7. To the polishing of the scintillator array base body 7, a lap polishing, for example, using diamond abrasive grains is applied. When the lap polishing was performed, the end portion of the hard scintillator block 2 is more likely to be polished than the soft reflective layer part 3. There also is a method in which the R-shaped portion is hardly formed, by performing gradual polishing while changing the number (size of abrasive grain) of the diamond abrasive grain. However, this method requires much time and cost. Hence, by performing polishing in a manner to make the shape of the R-shaped portion 9 fall within a predetermined size, it becomes possible to reduce the manufacturing cost of the scintillator array 1.

Figure 8:
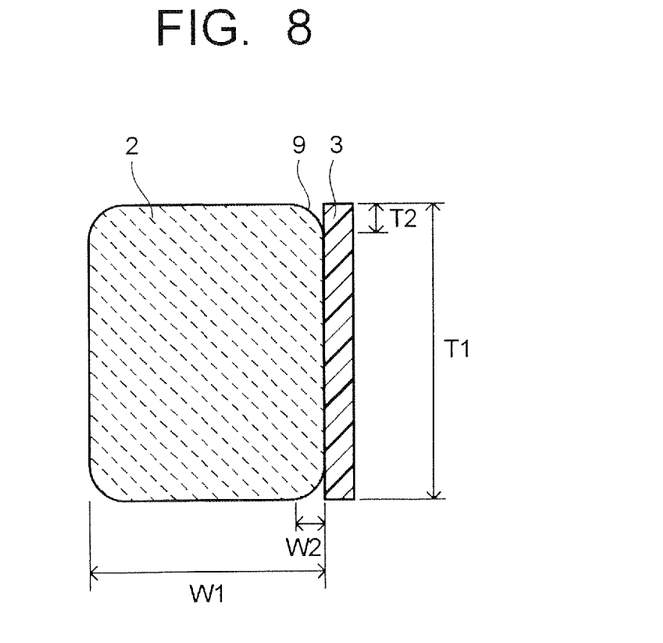
FIG. 8 is an enlarged cross-sectional view illustrating the shape of a corner portion of the scintillator array illustrated in FIG. 7.

FIG. 8 illustrated a concrete shape example of the R-shaped portion 9 of the scintillator block 2. In FIG. 8, T1 indicates the thickness of the scintillator block 2, T2 indicates the thickness of the R-shaped portion 9, W1 indicates the width of the scintillator block 2, and W2 indicates the width of the R-shaped portion 9. In the case where the scintillator block 2 has the R-shaped portion 9, the R-shaped portion 9 preferably has a shape satisfying W2/W1≤0.02 and a shape satisfying T2/T1≤0.02. If W2/W1 exceeds 0.02 or T2/T1 exceeds 0.02, the reflection characteristics between the scintillator block 2 and the reflective layer part 3 may become nonuniform. Further, in the case where the surface reflective layer 6 illustrated in FIG. 4 is provided, if the dispersion states of the reflective particles in the reflective layer part 3 and the surface reflective layer 6 are different from each other, the surface reflective layer 6 different in reflection characteristics enters into the R-shaped portion 9, causing variations in reflection characteristics. For this reason, the R-shaped portion 9 preferably has a shape satisfying W2/W1≤0.02 and T2/T1≤0.02, and more preferably has a shape satisfying W2/W1≤0.01 and T2/T1≤0.01.

Further, as necessary, the warpage repair process may be performed on the scintillator array 1 after the transparent resin is hardened. The warpage amount is preferably 0.2 mm or less in a long side direction and in a short side direction of the scintillator array 1, and more preferably 0.1 mm or less. If the warpage amount of the produced scintillator array 1 exceeds 0.2 mm, it is preferable to perform the warpage repair process. The warpage repair process of the scintillator array 1 can be a method of heat-treating it while pressing its upper and lower surfaces. In the case where the transparent resin is a thermosetting resin, the warpage repair can be carried out by applying both a pressing force and heat thereto. On at least one of the X-ray incident surface and the element mounting surface of the scintillator array 1, the surface reflective layer is formed as necessary.

Next, Examples and their evaluation results will be described.

EXAMPLE 1

As reflective particles, titanium oxide ($TiO_2$) powder having a mean particle diameter of 0.2 μm was prepared. The titanium oxide powder has a particle size distribution having a peak at 0.22 μm. The titanium oxide powder was loaded on the ultrasonic vibrator to break aggregates and then mixed with an epoxy resin as the transparent resin. The mixing process of the titanium oxide powder and the epoxy resin was carried out using the three roll mixing machine. The mixing time by the three roll mixing machine was set to 20 hours. The viscosity of the mixture of the titanium oxide powder and the epoxy resin (resin mixture) was set to 2 Pa·s.

Then, a scintillator block composed of the sintered compact of gadolinium oxysulfide ($Gd_2O_2S:Pr$) of 1 mm long×1 mm wide×1 mm thick was prepared. The scintillator block was polished to have a surface roughness (Ra) of 1 μm. The gaps between adjacent scintillator blocks were made uniform to 80 μm, and scintillator blocks were arranged such that 64 scintillator blocks were arranged in the long side direction and 24 scintillator blocks were arranged in the short side direction. The resin mixture was impregnated between the adjacent scintillator blocks. The impregnation process of the resin mixture was carried out in a vacuum of 4 kPa or less. Within three hours after the resin mixture was impregnated, a heat treatment was performed at a temperature of 100° C. to harden the epoxy resin (transparent resin).

EXAMPLES 2 to 5

Scintillator arrays were produced by applying the same method as that in Example 1 other than using the reflective particles having mean particle diameters and materials listed in Table 1

COMPARATIVE EXAMPLE 1

A scintillator array was produced by applying the same method as that in Example 1 other than not mixing the transparent resin with reflective particles. Comparative Example 1 includes a transparent resin layer containing no reflective particles.

COMPARATIVE EXAMPLE 2

A scintillator array was produced by applying the same method as that in Example 1 other than using $TiO_2$ powder having a mean particle diameter of 3 μm as the reflective particles.

COMPARATIVE EXAMPLE 3

A scintillator array was produced by applying the same method as that in Example 1 other than changing the mixture ratio between the titanium oxide powder and the epoxy resin and the mixture conditions. Comparative Example 3 is configured to have the number of the reflective particles existing per unit area of the reflective layer part outside the range of the present invention.

About the scintillator arrays in Examples 1 to 5 and Comparative Examples 1 to 3, the number of the reflective particles existing per unit area (5 μm×5 μm) of the reflective layer part, the area ratio of aggregates of the reflective particles per unit area (10 μm×10 μm), and the existing ratio of voids in the thickness direction of the reflective layer part were measured. These results are listed in Table 1. Further, the warpage amount of the scintillator array, the reflectance of the reflective layer part, and the optical output of the scintillator array were obtained. The results are listed in Table 2. The warpage amounts in the long side direction and in the short side direction of the scintillator array were measured, and the value of larger warpage was listed. As the optical output, a relative value when the optical output in Comparative Example 1 is 100 is listed.

TABLE 1

| | Reflective particle | | | Reflective layer part | | |
|---|---|---|---|---|---|---|
| | Material | Mean particle diameter [μm] | Particle size distribution *1 [μm] | Transparent resin | Number of reflective particles *2 | Area ratio of aggregates [%] *3 | Existing ratio of voids [%] |
| E1 | $TiO_2$ | 0.2 | 0.22 | Epoxy | 150 | 30 | 0.001 |
| E2 | $TiO_2$ | 0.1 | 0.13 | Epoxy | 150 | 30 | 0.002 |
| E3 | $TiO_2$ | 0.5 | 0.47 | Epoxy | 150 | 30 | 0.002 |
| E4 | $TiO_2$ | 0.8 | 0.78 | Epoxy | 100 | 20 | 0.005 |
| E5 | $Ta_2O_5$ | 1.3 | 1.41 | Epoxy | 100 | 20 | 0.005 |
| CE1 | No | — | — | Epoxy | — | — | 0.01 |

TABLE 1-continued

| | | Reflective particle | | | Reflective layer part | | |
|---|---|---|---|---|---|---|---|
| | Material | Mean particle diameter [μm] | Particle size distribution *1 [μm] | Transparent resin | Number of reflective particles *2 | Area ratio of aggregates [%] *3 | Existing ratio of voids [%] |
| CE2 | TiO$_2$ | 3.0 | 3.20 | Epoxy | 10 | 10 | 0.01 |
| CE3 | TiO$_2$ | 1.0 | 0.90 | Epoxy | 80 | 10 | 0.01 |

*1: Peak value of particle size distribution.
*2: Number of reflective particles per unit area (5 μm × 5 μm).
*3: Area ratio of aggregates of reflective particles per unit area (10 μm × 10 μm).
E1 to E5 = Example 1 to Example 5;
CE1 to CE 3 = Comparative Example 1 to Comparative Example 3

TABLE 2

| | Warpage amount [mm] | Reflectance of reflective layer part [%] | | Optical output |
|---|---|---|---|---|
| | | Wavelength of 510 mm | Wave length of 670 mm | |
| Example 1 | 0.01 | 96 | 93 | 200 |
| Example 2 | 0.02 | 94 | 92 | 192 |
| Example 3 | 0.01 | 94 | 92 | 190 |
| Example 4 | 0.02 | 93 | 90 | 186 |
| Example 5 | 0.02 | 93 | 90 | 186 |
| Comparative Example 1 | 0.02 | — | — | 100 |
| Comparative Example 2 | 0.03 | 86 | 84 | 123 |
| Comparative Example 3 | 0.02 | 90 | 88 | 146 |

As is clear from Table 2, the scintillator arrays in Examples 1 to 5 are excellent in optical output. Namely, even if the same scintillator block is used, the optical output of the scintillator array can be improved by controlling the dispersion state of the reflective particles in the reflective layer part.

EXAMPLE 6

As reflective particles, titanium oxide (TiO$_2$) powder having a mean particle diameter of 0.25 μm was prepared. The titanium oxide powder has a particle size distribution having a peak at 0.28 μm. The titanium oxide powder was loaded on the ultrasonic vibrator to break aggregates and then mixed with an epoxy resin as the transparent resin. The mixing process of the titanium oxide powder and the epoxy resin was carried out using the three roll mixing machine. The mixing time by the three roll mixing machine was set to 25 hours. The viscosity of the mixture of the titanium oxide powder and the epoxy resin (resin mixture) was set to 1.8 Pa·s.

Then, a scintillator block composed of the sintered compact of aluminum garnet (($Gd_{0.49}Tb_{0.20}Lu_{0.30}Ce_{0.01})_3(Al_{0.6}Ga_{0.4})_5O_{12}$) of 1 mm long×1 mm wide×1 mm thick was prepared. The scintillator block was polished to have a surface roughness (Ra) of 1 μm. The gaps between adjacent scintillator blocks were made uniform to 80 μm and scintillator blocks were arranged such that 64 scintillator blocks were arranged in the long side direction and 24 scintillator blocks were arranged in the short side direction. The resin mixture was impregnated between the adjacent scintillator blocks. The impregnation process of the resin mixture was carried out in a vacuum of 4 kPa or less. Within three hours after the resin mixture was impregnated, a heat treatment was performed at a temperature of 100° C. to harden the epoxy resin (transparent resin).

EXAMPLES 7 to 10

Scintillator arrays were produced by applying the same method as that in Example 6 other than using the reflective particles having mean particle diameters listed in Table 3.

COMPARATIVE EXAMPLE 4

A scintillator array was produced by applying the same method as that in Example 6 other than not mixing the transparent resin with reflective particles. Comparative Example 6 includes a transparent resin layer containing no reflective particles.

COMPARATIVE EXAMPLE 5

A scintillator array was produced by applying the same method as that in Example 6 other than using TiO$_2$ powder having a mean particle diameter of 3 μm as the reflective particles.

About the scintillator arrays in Examples 6 to 10 and Comparative Examples 4 to 5, the number of the reflective particles existing per unit area (5 μm×5 μm) of the reflective layer part, the area ratio of aggregates of the reflective particles per unit area (10 μm×10 μm), and the existing ratio of voids in the thickness direction of the reflective layer part were measured. These results are listed in Table 3. Further, the warpage amount of the scintillator array, the reflectance of the reflective layer part, and the optical output of the scintillator array were obtained. The results are listed in Table 4. The measurement was carried out similarly in Example 1.

TABLE 3

| | | Reflective particle | | | Reflective layer part | | |
|---|---|---|---|---|---|---|---|
| | Material | Mean particle diameter [μm] | Particle size distribution *1 [μm] | Transparent resin | Number of reflective particles *2 | Area ratio of aggregates [%] *3 | Existing ratio of voids [%] |
| E6 | TiO$_2$ | 0.2 | 0.22 | Epoxy | 140 | 28 | 0.002 |
| E7 | TiO$_2$ | 0.1 | 0.13 | Epoxy | 180 | 30 | 0.002 |

TABLE 3-continued

| | Reflective particle | | | | Reflective layer part | | |
|---|---|---|---|---|---|---|---|
| | Material | Mean particle diameter [μm] | Particle size distribution *1 [μm] | Transparent resin | Number of reflective particles *2 | Area ratio of aggregates [%] *3 | Existing ratio of voids [%] |
| E8 | TiO$_2$ | 0.5 | 0.47 | Epoxy | 150 | 25 | 0.003 |
| E9 | TiO$_2$ | 0.8 | 0.78 | Epoxy | 110 | 17 | 0.001 |
| E10 | Ta$_2$O$_5$ | 1.3 | 1.41 | Epoxy | 100 | 20 | 0.010 |
| CE4 | No | — | — | Epoxy | — | — | 0.01 |
| CE5 | TiO$_2$ | 3.0 | 3.20 | Epoxy | 10 | 10 | 0.01 |

*1: Peak value of particle size distribution.
*2: Number of reflective particles per unit area (5 μm × 5 μm).
*3: Area ratio of aggregates of reflective particles per unit area (10 μm × 10 μm).
E6 to E10 = Example 6 to Example 10;
CE4 to CE5 = Comparative Example 4 to Comparative Example 5

TABLE 4

| | Warpage amount [mm] | Reflectance of reflective layer part [%] | | Optical output |
|---|---|---|---|---|
| | | Wavelength of 510 mm | Wave length of 670 mm | |
| Example 6 | 0.02 | 95 | 92 | 210 |
| Example 7 | 0.02 | 92 | 91 | 195 |
| Example 8 | 0.01 | 94 | 92 | 190 |
| Example 9 | 0.01 | 93 | 91 | 185 |
| Example 10 | 0.02 | 93 | 90 | 187 |
| Comparative Example 4 | 0.02 | — | — | 100 |
| Comparative Example 5 | 0.02 | 86 | 84 | 125 |

As is clear from Table 4, the scintillator arrays in Examples 6 to 10 are excellent in optical output. Namely, even if the same scintillator block is used, the optical output of the scintillator array can be improved by controlling the dispersion state of the reflective particles in the reflective layer part.

EXAMPLES 1A to 10A

A surface reflective layer having the same dispersion state of the reflective particles as in the reflective layer part was formed on one surface of each of the scintillator arrays in Examples 1 to 10, and the optical output was obtained. The results are listed in Table 5. The optical output is a relative value when the optical output in Comparative Example 1 is 100, for Examples 1A to 5A, and a relative value when the optical output in Comparative Example 4 is 100, for Examples 6 to 10. The thickness of the surface reflective layer was set to 100 μm, for Examples 1A to 5A, and the thickness of the surface reflective layer was set to 150 μm, for Examples 6A to 10A.

TABLE 5

| | Scintillator array formed with surface reflective layer | Optical output |
|---|---|---|
| Example 1A | Example 1 | 260 |
| Example 2A | Example 2 | 255 |
| Example 3A | Example 3 | 247 |
| Example 4A | Example 4 | 240 |
| Example 5A | Example 5 | 242 |
| Comparative Example 1 | Comparative Example 1 | 100 |
| Example 6A | Example 6 | 270 |
| Example 7A | Example 7 | 260 |
| Example 8A | Example 8 | 256 |
| Example 9A | Example 9 | 252 |
| Example 10A | Example 10 | 250 |
| Comparative Example 4 | Comparative Example 4 | 100 |

As is clear from Table 5, the optical output is further improved by providing the surface reflective layer. As described above, any of the scintillator arrays according to Examples is improved in optical output. Accordingly, the scintillator arrays, when applied to the X-ray examination device such as the X-ray CT device, can improve the examination accuracy and can shorten the measuring time, namely, realize reduced radiation exposure.

EXAMPLES 11 to 15

As a scintillator block base body, a sintered compact of gadolinium oxysulfide (Gd$_2$O$_2$S:Pr) of 100 mm long×40 mm wide×1.2 mm thick was prepared. The scintillator block base body was subjected to wire saw process to have block sizes and groove shapes as listed in Table 6.

TABLE 6

| | Size of scintillator block (length [mm] × width [mm] × thickness [mm]) | Width of groove part [μm] |
|---|---|---|
| Example 11 | 1.0 × 1.0 × 1.0 | 60 |
| Example 12 | 1.0 × 1.0 × 1.0 | 50 |
| Example 13 | 1.0 × 1.0 × 1.0 | 40 |
| Example 14 | 0.9 × 0.9 × 0.9 | 70 |
| Example 15 | 0.9 × 0.9 × 0.9 | 50 |

As reflective particles, titanium oxide (TiO$_2$) powder having a mean particle diameter of 0.2 μm was prepared. The titanium oxide powder has a particle size distribution having a peak at 0.22 μm. The titanium oxide powder was loaded on the ultrasonic vibrator to break aggregates and then mixed with an epoxy resin as the transparent resin. The mixing process of the titanium oxide powder and the epoxy resin was carried out using the three roll mixing machine. The mixing time by the three roll mixing machine was set to 10 hours to 50 hours. The viscosity of the mixture of the titanium oxide powder and the epoxy resin (resin mixture) was adjusted to values listed in Table 7.

The resin mixture adjusted in viscosity was applied to the surface of the scintillator block base body formed with groove parts. Then, the resin mixture was filled into the groove parts using the centrifuge. The filling conditions of the resin mixture are as listed in Table 7. After, the resin mixture was filled into the groove parts, a heat treatment was performed thereon to harden the epoxy resin (transparent resin). Thereafter, the scintillator block base body having the reflective layer parts was subjected to polishing using diamond abrasive grains. The conditions of the polishing are as listed in Table 7.

TABLE 7

|  | Resin mixture | Filling process | | Polishing process |
| --- | --- | --- | --- | --- |
|  | Viscosity [Pa·s] | Atmosphere | Number of rotations of centrifuge [rpm] | Number of abrasive grain |
| Example 11 | 2.5 | Vacuum (1.3 kPa) | 700 | 400 |
| Example 12 | 2.0 | Vacuum (4 kPa) | 1000 | 600 |
| Example 13 | 1.8 | Vacuum (4 kPa) | 1500 | 2000 |
| Example 14 | 1.0 | Vacuum (1.3 kPa) | 2000 | 2500 |
| Example 15 | 0.5 | Vacuum (1.3 kPa) | 1100 | 3000 |

About the obtained scintillator arrays, the shape of the scintillator block was evaluated. At the end portion of the scintillator block, an R-shaped portion was formed. The surface roughness (Ra) and the shape of the R-shaped portion of the scintillator block were measured. These results are listed in Table 8. Further, when the warpage amount of the scintillator array was measured, the warpage amount of any of them was less than 0.01 mm. Therefore, the warpage repair process for the scintillator array was unnecessary.

TABLE 8

|  | Scintillator block | | |
| --- | --- | --- | --- |
|  | Surface roughness | R-shape of end portion | |
|  | Ra [μm] | W2/W1 | T2/T1 |
| Example 11 | 0.050 | 0.013 | 0.014 |
| Example 12 | 0.031 | 0.009 | 0.008 |
| Example 13 | 0.022 | 0.008 | 0.008 |
| Example 14 | 0.020 | 0.007 | 0.007 |
| Example 15 | 0.017 | 0.007 | 0.006 |

About the scintillator arrays in Examples 11 to 15, the number of the reflective particles existing per unit area (5 μm×5 μm) of the reflective layer part, the area ratio of aggregates of the reflective particles per unit area (10 μm×10 μm), the reflectance of the reflective layer part, and the optical output of the scintillator array were measured. The results are listed in Table 9. The measurement was carried out similarly in Example 1.

TABLE 9

| | Reflective layer part | | | | |
| --- | --- | --- | --- | --- | --- |
| | Number of reflective particles *2 | Area ratio of aggregates *3 | Reflectance [%] | | Optical output |
| | | | Wavelength of 510 nm | Wavelength of 670 nm | |
| Example 11 | 120 | 20 | 94 | 92 | 180 |
| Example 12 | 150 | 10 | 95 | 93 | 210 |
| Example 13 | 160 | 7 | 96 | 94 | 210 |

TABLE 9-continued

| | Reflective layer part | | | | |
| --- | --- | --- | --- | --- | --- |
| | Number of reflective particles *2 | Area ratio of aggregates *3 | Reflectance [%] | | Optical output |
| | | | Wavelength of 510 nm | Wavelength of 670 nm | |
| Example 14 | 160 | 7 | 96 | 93 | 200 |
| Example 15 | 180 | 5 | 96 | 94 | 210 |

*2: Number of reflective particles per unit area (5 μm × 5 μm)
*3: Area ratio of aggregates of reflective particles per unit area (10 μm × 10 μm)

As is clear from Table 9, the scintillator arrays in Examples 11 to 15 are excellent in optical output. Further, scintillator arrays in Examples 11 to 15 are manufactured using the scintillator block base body and therefore excellent in mass productivity.

EXAMPLES 11A to 15A

A surface reflective layer having the same dispersion state of the reflective particles as in the reflective layer part was formed on one surface of each of the scintillator arrays in Examples 11A to 15A, and the optical output was obtained. The results are listed in Table 10. The optical output is a relative value when the optical output in Comparative Example 1 is 100. The thickness of the surface reflective layer was set to 100 μm, for Examples 1A to 5A, and the thickness of the surface reflective layer was set to 150 μm, for Examples 6A to 10A.

TABLE 10

| | Scintillator array formed with surface reflective layer | Optical output |
| --- | --- | --- |
| Example 11A | Example 11 | 245 |
| Example 12A | Example 12 | 260 |
| Example 13A | Example 13 | 260 |
| Example 14A | Example 14 | 255 |
| Example 15A | Example 15 | 260 |
| Comparative Example 1 | Comparative Example 1 | 100 |

As is clear from Table 10, the optical output is further improved by providing the surface reflective layer. As described above, any of the scintillator arrays according to Examples is improved in optical output. Accordingly, the scintillator arrays, when applied to the X-ray examination device such as the X-ray CT device, can improve the examination accuracy and can shorten the measuring time, namely, realize reduced radiation exposure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A scintillator array, comprising:
a plurality of scintillator blocks; and
a reflective layer part, interposed between adjacent scintillator blocks to integrate the plurality of scintillator blocks, the reflective layer part comprising a transparent resin and reflective particles dispersed in the transparent resin, wherein the reflective particles include at least one type of particle selected from the group consisting of titanium oxide particles and tantalum oxide particles, and have a mean particle diameter of 2 μm or less;

wherein a number of the reflective particles existing per unit area of 5 μm×5 μm of the reflective layer part is in a range of 100 or more and 250 or less;

wherein each of the scintillator blocks has an R-shaped portion at an end portion thereof, and the R-shaped portion has a shape wherein a ratio of a width W2 of the R-shaped portion to a width W1 of the scintillator block is in a range of 0.007 to 0.02, and a ratio of a thickness T2 of the R-shaped portion to a thickness T1 of the scintillator block is in a range of 0.006 to 0.02; and wherein a warpage amount of the scintillator array is 0.2 mm or less.

2. The scintillator array according to claim 1, wherein an area ratio of aggregates of the reflective particles per unit area of 10 μm×10 μm of the reflective layer part is 40% or less (including 0%).

3. The scintillator array according to claim 1, wherein the reflective layer part is directly bonded to each of the adjacent scintillator blocks.

4. The scintillator array according to claim 1, wherein an existing ratio of voids in a cross section in a thickness direction of the reflective layer part is 1% or less.

5. The scintillator array according to claim 1, wherein the scintillator block has a surface roughness in arithmetic mean roughness Ra of 5 μm or less.

6. The scintillator array according to claim 1, wherein the scintillator block includes at least one selected from the group consisting of a gadolinium oxysulfide sintered compact and an aluminum garnet sintered compact.

7. The scintillator array according to claim 1, wherein the mean particle diameter of the reflective particles is 1 μm or less.

8. The scintillator array according to claim 1, wherein the transparent resin comprises an epoxy resin.

9. The scintillator array according to claim 1, wherein a reflectance of the reflective layer part to light with a wavelength of 510 nm is 93% or more.

10. The scintillator array according to claim 1, wherein a reflectance of the reflective layer part to light with a wavelength of 670 nm is 90% or more.

11. The scintillator array according to claim 1, further comprising:
a surface reflective layer provided at least on one surface of the scintillator array.

12. An X-ray detector comprising the scintillator array according to claim 1.

13. An X-ray examination device comprising the X-ray detector according to claim 12.

* * * * *